United States Patent [19]

Takematsu et al.

[11] 4,265,654

[45] May 5, 1981

[54] HERBICIDAL COMPOSITIONS

[75] Inventors: Tetsuo Takematsu; Makoto Konnai, both of Utsunomiya; Kunitaka Tachibana, Yokohama; Takashi Tsuruoka, Kawasaki; Shigeharu Inouye; Tetsuro Watanabe, both of Yokohama, all of Japan

[73] Assignee: Meiji Seika Kaisha Ltd., Tokyo, Japan

[21] Appl. No.: 971,636

[22] Filed: Dec. 20, 1978

[30] Foreign Application Priority Data

Dec. 28, 1977 [JP] Japan .................................. 52-157421
Dec. 28, 1977 [JP] Japan .................................. 52-157422
Dec. 29, 1977 [JP] Japan .................................. 52-158932
Mar. 30, 1978 [JP] Japan .................................. 53-36059

[51] Int. Cl.$^3$ ............................................. A01N 57/12
[52] U.S. Cl. ......................................... 71/86; 71/92; 71/94; 71/115; 71/120
[58] Field of Search ............................................. 71/86

[56] References Cited

FOREIGN PATENT DOCUMENTS 4914644 of 0000 Japan.

OTHER PUBLICATIONS

Ogawa et al., Chem. Abst., vol. 80 (1974) 60035b.
Rupp et al., Ger. Offen. 2,717,440 (12-01-77), Chem. Abst., vol. 88 (1978) 70494e.

*Primary Examiner*—Catherine L. Mills
*Attorney, Agent, or Firm*—Frishauf, Holtz, Goodman & Woodward

[57] ABSTRACT

2-Amino-4-methylphosphinobutyric acid or its metal salts, or acid-addition salts thereof are used as perennial weeds and brush controlling agents. The L-isomer is twice effective than the racemic acid. The perennial weeds and brush controlling effect may be obtained by foliar application over a prolonged period.

11 Claims, No Drawings

HERBICIDAL COMPOSITIONS

The invention relates to herbicidal compositions and methods for controlling perennial weeds and brush.

More particularly, it relates to the application of herbicidal compositions for controlling perennial weeds and brush which comprise a compound represented by formula (I):

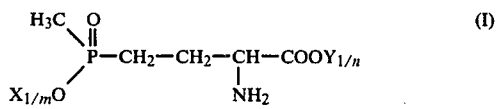

wherein, X and Y are same or different and each represents hydrogen atom, mono- or divalent metal atom, ammonium, mono-, di- or tri-lower alkylammonium, mono-, di- or tri-ethanolammonium or mono-, di- or tri-lower alkenylammonium or an acid-addition salt thereof.

It also relates to herbicidal compositions for controlling perennial weeds and brush which comprises an L-isomer of the compound of formula (I) or an acid-addition salt thereof and to the application thereof.

It further relates to herbicidal compositions for controlling perennial weeds and brush which comprise a compound of formula (I) or an acid-addition salt thereof and a herbicide or herbicides selected from the group consisting of choline a salt of maleic hydrazide, a phenoxy series herbicide, a benzoic acid series herbicide, 2,3,6-trichlorophenylacetic acid or a salt thereof, (3,5,6-trichloro-2-pyridyl)oxy-acetic acid or a salt thereof, N-phosphonomethylglycine or a salt thereof, ethylcarbamoylphosphoric acid or a salt thereof, 2-(1-allyloxyaminobutylidene)-5,5-dimethyl-4-methoxycarbonylcyclohexane-1,3-dione, 3-(3,4-dichlorophenyl)-1-methoxy-1-methylurea, 3-amino-1,2,4-triazole, choline or a salt thereof, and diethylamine or a salt thereof and to the application thereof.

It still further relates to herbicidal compositions for controlling perennial weeds and brush which comprise an L-isomer of the compound of formula (I) or an acid-addition salt thereof and a herbicide or herbicides recited above and to the application thereof.

In this specification, mono- or di-valent metal atom means, for example, sodium, potassium, lithium, copper, magnesium, calcium, zinc, nickel and manganese atom.

Lower alkylammonium means an alkylammonium having from 1 to 5 carbon atoms such as methylammonium, ethylammonium, propylammonium, isopropylammonium, butylammonium, isobutylammonium and pentylammonium.

Di-lower alkylammonium includes, for example, dimethylammonium, diethylammonium, dipropylammonium, diisopropylammonium, dibutylammonium and dipentylammonium.

Lower alkenylammonium contain in its respective alkenyl groups, for example, 3 or 4 carbon atoms and a double bond.

Acids which form a salt with the compound of formula (I) include inorganic acids such as hydrochloric acid, sulfuric acid, hydrobromic acid, phosphoric acid, perchloric acid and nitric acid, and organic acids such as acetic acid, propionic acid, citric acid, tartaric acid, chloroacetic acid, trichloroacetic acid and trifluoroacetic acid.

Cholines mean choline and salts thereof with an inorganic acid such as hydrochloric acid, phosphoric acid or carbonic acid, or with an organic acid such as acetic acid, oxalic acid or ascorbic acid.

Diethylamines mean diethylamine and salts thereof with an inorganic acid such as hydrochloric acid, phosphoric acid or carbonic acid, or with an organic acid such as acetic acid, oxalic acid or ascorbic acid.

Phenoxy series herbicides include, for example, 2,4-dichlorophenoxyacetic acid or salts or esters such as allyl ester or ethyl ester thereof, 2-methyl-4-chlorophenoxyacetic acid or salts or esters such as allyl ester or ethyl ester thereof, α-(3,4-dichlorophenoxy)propionic acid or salts thereof, 2-(2-methyl-4-chlorophenoxy)propionic acid or salts thereof, γ-(2-methyl-4-chlorophenoxy)butyric acid or salts thereof, 2-(2,4,5-trichlorophenoxy)propionic acid or salts thereof and α-[4-(3,5-dichloropyridyl-2-oxy)phenoxy]propionic acid or salts thereof.

Benzoic acid series herbicides include, for example, 2,3,6-trichlorobenzoic acid or salts thereof, 3,6-dichloro-2-methoxybenzoic acid or salts thereof and 3-amino-2,5-dichlorobenzoic acid or salts thereof.

In recent years, the growth of perennial weeds has been increasing in paddy field, upland, orchard and meadow.

The propagation of perennial weeds by means of their undergound part is so rapid and strong that it may not readily be controlled. In crop land, they propagate with their clonal propagation organ of the underground part finely divided and distributed by cultivation, agitation and movement of soil. As perennial weeds are generally large in size and propagate fluorishingly and own the basis of life under the ground, they predominate over crops in the competition for nutrients, water and light. Heretofore, N-phosphonomethylglycine (hereinafter referred to as glyphosate) is known as the controlling agent for perennial weeds; but it has a disadvantage in that it is not particularly effective for broad-leaved weeds. Therefore, there have been desired controlling agents against a broad spectrum of weeds. It has been also a serious problem to control brush in non-crop land, meadow and forest land. For instance, large perennial weeds such as miyakozasa (*Sasa nipponica* Makino et Shibata) and eulalia (*Miscanthus sinensis* Andress.) and brush such as kumaichigo (*Rubus crataegifolius* Bunge), chestnut (*Castanea crenata* Sieb et Zucc.) and Japanese bush cranberry (*Viburnum dilatatum* Thunb.) predominate over Japanese cedar (*Cryptomeria japonica* D. Don) and Japanese cypress (*Chamaecyparis obtusa* Endl.) in forest land in the competition for nutrients, water and light. Also at meadow, the control of brush around there is a problem.

There are few herbicides effective for brush because of difficulty in controlling it. Namely, unlike herbaceous plants, brush has a hard bark to prevent the penetration of a controlling agent; it is generally larger than herbaceous plants; and it has a developed reproduction mechanism, or branches even after defoliation.

While known herbicides are all synthetic substances, there have been desired readily degradable herbicides in view of environmental pollution. 2-amino-4-methylphosphinobutyric acid, which is one of the compounds represented by formula (I) and hereinafter referred to as AMPB, as an antibiotic substance obtained by the methods disclosed in Japanese Patent Publication Specifications Nos. 48-85538 and 49-31890, as laid open to public inspection and entitled "Novel method of producing α-amino-γ-methylphosphinobutyric acid". The compound has the above mentioned desirable characteristic that is metabolized and degraded safely in nature's cycle.

AMPB is known to control a wide variety of phytopathogenic microorganisms at a low concentration and may be used as an agricultural fungicide, as disclosed in Japanese Patent Publication Specification No. 49-14644 as laid open to public inspection. After further studies on the biological activities and utilities of the substance, it has been found that it has a superior herbicidal activity when applied to about ten times higher concentration than for controlling phytopathogenic microorganisms. Namely, AMPB is effective for controlling growing perennial weeds and brush by killing the underground part by foliar application and by strong inhibiting reproduction. The inventors have found, after detailed investigation of the characteristics of the action of AMPBs against perennial weeds and brush for a long period, that AMPBs possess contact killing effect, and at the same time, the following superior characteristics. To wit, when AMPBs are applied to foliage of perennial weeds, they move to the underground part such as rhizome, tuber, bulb, corm or root which is the basis of life of perennial weeds and kill the underground part.

As the results, perennial weeds are controlled by foliar application, preventing reproduction by the underground part. This has been an immportant but difficult problem to solved. Similarly, brush is controlled by foliar application of AMPBs which move to every part of the brush, thus killing it and preventing reproduction thereof. The newly found reproduction-preventing effect of AMPBs against perennial weeds and brush makes AMPBs advantageous over glyphosate.

For instance, while glyphosate shows poor controlling effect against broad-leaved perennial weeds, AMPBs show quite broad spectrum effect and control against almost all perennial weeds.

Further, AMPBs show quicker penetration and absorption into plants, better resistance to rainfall and control is effected more rapidly than when using glyphosate. Although known contact herbicides may kill perennial weeds and brush at their juvenile stage, they fail to control them when the underground part develops and reproduction takes place.

Contrary to this, it was confirmed that AMPBs may kill large weeds and brush. Furthermore, there has been no previous knowledge of the selective herbicidal activity of AMPBs. The inventors have found, after testings for various crops and trees, that Japanese cypress which is a useful tree and occupies 25 percent of forest land in Japan is quite resistant to AMPBs and that AMPBs may be used for controlling bottom weeds in Japanese cypress forest land to kill perennial weeds and brush and inhibit their reproduction over a long period of time.

Perennial weeds and brush may be found generally in non-crop land, orchard, forest land and meadow. As mentioned above, AMPBs have a strong activity against almost all of perennial weeds and brush, except Japanese cypress, and therefore, they may be used alone particularly to control and prevent the reproduction of perennial weeds and brush.

Accordingly, AMPBs may be used for the development of forest land and bottom weeds control of perennial weeds and brush in Japanese cypress forest land. They may also be used at meadow, orchard and non-crop land for controlling perennial weeds and brush. Further, they may be effectively used in a paddy field for controlling perennial lowland weeds. Furthermore, they may be used upland for controlling perennial weeds before sowing, as they may be inactivated in soil comparatively rapidly.

As is clear in formula (I), AMPB has an asymmetric carbon atom at 2-position, and therefore, there exist stereo-isomers. After further studies of upperground part-killing activity and reproduction-inhibiting activity of AMPBs, the inventors have found that L-isomer of AMPB (hereinafter referred to as L-AMPB) has twice the activity of AMPB (hereinafter some times referred to as DL-AMPB) and that the essence of the herbicidal activity of DL-AMPB resides in L-AMPB. The mode of action of DL-AMPB has been studied by using microorganisms and it has been clear that DL-AMPB inhibits glutamine synthetase competitively [Helevetica Chemica Acts, 55, Fase 1, pp 224–239 (1972)]. It may be considered that DL-AMPB is taken into the enzyme in place of the substrate as a kind of unusual amino acid and suspends the function of the enzyme, thus exhibiting the herbicidal activity.

As generally recognized, naturally occuring amino acids are all L-form, and enzymes comprising the amino acids have a high specificity. It is therefore presumed that, among DL-AMPB, L-AMPB is taken into the enzyme in place of the substrate and exhibits herbicidal activity. The presumption coincides with the fact that L-AMPB is twice as effective as DL-AMPB, as found by the inventors.

The amount of AMPBs needed for killing and inhibiting reproduction of perennial weeds and brush will vary, depending on climatic conditions such as temperature and light intensity, and species of weeds and woody weeds to be treated.

DL-AMPBs are usually applied in amounts of 50 g./10 are to 1200 g./10 are to perennial weeds of less than 1 meter height, such as wormwood (*Artemisia princeps*), curly dock (*Rumex japonicus* Houtt.) and purple nutsedge (*Cyperus rotundus* L.); 150 g./10 are to 1500 g./10 are to perennial weeds of more than 1 meter height, such as miyakozasa and eulalia, and small brush such as torch azalea (Rhododendron Kaempferi Planch.) and kumaichigo; and 300 g./10 are to 3000 g./10 are to large brush, such as chestnut and oak (*Quercus serrata* Thunb), and to large stump for controlling the emergence of new buds, by which perennial weeds and woody weeds may be killed and the reproduction thereof may be prevented. The treatment may be possible throughout year, but it is generally performed in spring or summer at growing stage, or in autumn.

As a result of our investigation to make the best use of the characteristics of the herbicidal composition according to the invention, we have found that, on application of the composition according to the invention to foliage and stems of perennial weeds and brush in autumn, the emergence of new buds of perennial weeds and brush would be strongly controlled in the next spring (see Tables 12 through 16), and thus succeeded in broadening the range of seasons over which the composition according to the invention appropriately is employed, by using the method mentioned above. While the appropriate seasons for treatment by ordinary herbicidal composition are mainly from spring to summer and a herbicide suitable for treatment in autumn has been limited to DPX-1108 etc., the invention provides a newly discovered composition which is excellent for treatment in autumn.

The following are examples of compounds of formula (I) and acid-addition salts thereof to be employed in the invention: AMPB; its sodium, potassium, lithium, ammonium, magnesium, calcium, nickel, manganese, zinc, copper, methylammonium, ethylammonium, propylammonium, isopropylammonium, n-butyl-ammonium, allylammonium and ethanolammonium salts, and the corresponding di-salts; and its hydrochloric, hydrobromic, nitric, perchloric, sulfuric, acetic, propionic, citric, tartaric, chloroacetic, trichloroacetic and trifluoroacetic acid salts.

Thereof, AMPB and its sodium, disodium, potassium, dipotassium, isopropylammonium, n-butylammonium and diammonium salts are preferred.

From the foregoing description, it is to be understood that L-AMPB and the salts thereof are especially preferred.

Although AMPBs, particularly L-AMPs show a strong reproduction-inhibiting activity by foliar application besides contact killing activity, the effect is not necessarily satisfactory depending on circumstances. In order to utilize the above mentioned superior characteristics of AMPBs, the inventors have further investigated and found that the translocating weeding effect, i.e. reproduction-inhibiting effect of AMPBs, which is one of their characteristics, could be surprisingly enhanced by using them together with a translocating herbicide or slow acting type herbicide, or with a synergist such as choline or diethylamine. For instance, as shown in Table 4, 0.025% of monosodium salt of L-AMPB kills 40% of bitter dock (*Rumex obtusifolius* L.) but fails to inhibit its reproduction.

0.1% of 2,4-dichlorophenoxyacetic acid (hereinafter referred to as 2,4-D) brings about the curvature of foliage of bitter dock but fails to kill it or inhibit its reproduction. Contrary to these, a mixture of 0.025% of monosodium salt of L-AMPB and 0.1% of 2,4-D exhibits a synergistic effect and kills bitter dock thoroughly, thus inhibiting its reproduction completely. Similar effects may be observed in case of noshiba (*Zoysia japonica* Steud.) which is a perennial weed of Family Gramineae. Namely, 0.05% of monosodium salt of L-AMPB kills 50% of noshiba, which is reproduced three months after the treatment to such an extent that is comparable to non-treated area. 0.1% of 2,4-D is almost ineffective for controlling gramineous weeds. Contrary to these, a mixture of 0.05% of monosodium salt of L-AMPB and 0.1% of 2,4-D enhances the activity of the former remarkably and kills the uppground part throughly. No reproduction is observed at all three months after the treatment. Thus, substances having auxinlike activity represented by 2,4-D enhance the contact killing activity and translocating killing activity of L-AMPB, when admixed therewith, against both broad-leaved and narrow-leaved perennial weeds, especially with respect to reproduction-inhibiting activity.

Similar results may be obtained using the choline salt of maleic acid hydrazide (hereinafter referred to as CMH).

Namely, 0.3% of CMH itself shows almost no effect of killing the upperpart and inhibiting the reporduction of bitter dock. Whereas, a mixture of 0.3% of CMH and 0.05% of the monosodium salt of AMPB kills about 90% of the uppground part and yellows the remaining leaves which lose the activity and cease the subsequent growth, thus showing no reproduction. In general, the effect of L-AMPB may be enhanced from two to five times when used in combination with CMH.

Similar results may be obtained by using mixtures of AMPBs with a translocating herbicide or with choline or diethylamine as the synergist, enhancing the effect of AMPBs surprisingly.

Another characteristic of mixtures of AMPBs with the above mentioned herbicides or synergists is to broaden the species of weeds whose reproduction is inhibited. In order for AMPBs to show the characteristics of inhibiting the reproduction at their maximum, it is essential that they translocate to the underground part, after the foliar treatment and before the death of the upperground part.

However, in case of weeds showing a rapid killing effect such as hedge bindweed (*Calystegis hederacea* Wall.), the foliage gets killed before the translocation of AMPBs, thus making it difficult to inhibit the reproduction at the underground part. When AMPBs are used together with the translocated herbicide or slow acting herbicide mentioned above, they enhance the effect of the herbicides, and as the result, exhibit a superior reproduction-inhibiting effect against far broader species of weeds than use of AMPBs alone.

Among mixtures of the invention, the mixture of AMPBs with CMH is most excellent in view of its broad weeding spectrum and the thoroughness of its effect.

CMH is known to control perennial weeds by autumn treatment, as disclosed in Japanese Patent Publication Specification No. 49-55835, as laid open to public inspection.

However, a practical defect of CMH is that the timely treatment therewith is restricted to autumn and that cutting of upperground part is required after treatment when it is used in spring or summer. If CMH is used in combination with AMPBs, the latter kill the upperground part gradually, during which period both active ingredients are translocated to underground part and kill it by a synergistic action. Thus, the reproduction-inhibiting activity of CMH may be exhibited at its maximum and the timeliness of treatment therewith may be extended throughout the year. The practical utility of CMH has thus been improved.

Still another characteristic of mixtures of AMPBs with herbicides mentioned above is that they are quite effective for controlling bottom weeds of Japanese cypress forest land, particularly perennial weeds and brush.

In particular, both CMH and AMPBs show no phytotoxicity to Japanese cypress, and therefore, the combination is quite useful for the practical control of bottom weeds of Japanese cypress afforested land.

As described above, the joint use of AMPBs with the herbicides mentioned above brings about practical preferable characteristics, based upon which the following usages may be considered. Namely, mixtures of AMPBs, with the herbicides may be used for controlling a wide variety of annual weeds, perennial weeds and brush, particularly perennial lowland weeds in paddy fields after harvesting; perennial weeds in upland before sowing; perennial weeds and brush in forest land to enable planting; perennial weeds and brush in meadow; perennial weeds and brush in non-crop land such as factory, railroad, park, public facilities, riverbed, bank, highway, golf links and resting crop land; and water weeds and algae by means of foliar application in water.

Like CMH, ammonium ethylcarbamoylphosphate (hereinafter referred to as DPX-1108), cholines and diethylamines exhibit no phytotoxicity to Japanese cypress, and therefore, may be used in combination with AMPBs to control bottom weeds of Japanese cypress forest land. The mixture of AMPBs and CMH is also very useful for controlling perennial weeds in upland before sowing which are difficult to be controlled.

When AMPBs or L-AMPBs are mixed with other herbicide recited above, the ratio will vary from 1:0.1–20 by weight; but it will vary depending on the herbicide to be mixed therewith, as indicated in the following Table 1. Upon application, the composition may be diluted with water to a concentration indicated in the Table and treated at a rate of from 25 to 250 liter per 10 are, preferably from 50 to 150 liter per are.

TABLE 1

| Composition | Mixing ratio (wt.) | Application concentration (%) |
| --- | --- | --- |
| AMPBs | 1 | 0.01–1.0 |
| AMPBs:CMH | 1:1.0–10.0 | 0.01–1.0:0.2–1.0 |
| AMPBs:NP-48 | 1:0.5–5.0 | 0.01–1.0:0.05–0.5 |
| AMPBs:SL-501 | 1:0.5–5.0 | 0.01–1.0:0.05–0.5 |
| AMPBs:2,4-D | 1:0.2–4.0 | 0.01–1.0:0.05–0.4 |
| AMPBs:Dowco-233 | 1:0.1–3.0 | 0.01–1.0:0.02–0.2 |
| AMPBs:linuron | 1:0.4–4.0 | 0.01–1.0:0.05–0.5 |
| AMPBs:DPX-1108 | 1:0.5–5.0 | 0.01–1.0:0.1–0.6 |
| AMPBs:glyphosate | 1:0.3–3.0 | 0.01–1.0:0.03–0.5 |
| AMPBs:cholines | 1:1.0–2.4* | 0.01–1.0:0.01–0.8 |
| AMPBs:diethylamines | 1:1.0–2.4* | 0.01–1.0:0.01–0.5 |
| L-AMPBs:CMH | 1:1.0–20.0 | 0.005–0.5:0.005–10.0 |
| L-AMPBs:2,4-D | 1:0.3–8.0 | 0.005–0.5:0.0015–4.0 |
| L-AMPBs:MCP | 1:0.3–8.0 | 0.005–0.5:0.0015–4.0 |
| L-AMPBs:3,4-DP | 1:0.5–8.0 | 0.005–0.5:0.0025–4.0 |
| L-AMPBs:MCPP | 1:0.3–8.0 | 0.005–0.5:0.0015–4.0 |
| L-AMPBs:MCPB | 1:0.3–8.0 | 0.005–0.5:0.0015–4.0 |
| L-AMPBs:2,4,5-T | 1:0.3–8.0 | 0.005–0.5:0.0015–4.0 |
| L-AMPBs:SL-501 | 1:0.5–10.0 | 0.005–0.5:0.0025–5.0 |
| L-AMPBs:2,3,6-TBA | 1:0.3–8.0 | 0.005–0.5:0.0015–4.0 |
| L-AMPBs:Banvel-D | 1:0.3–8.0 | 0.005–0.5:0.0015–4.0 |
| L-AMPBs:amiben | 1:0.3–8.0 | 0.005–0.5:0.0015–4.0 |
| L-AMPBs:TPA | 1:0.3–8.0 | 0.005–0.5:0.0015–4.0 |
| L-AMPBs:Dowco-233 | 1:0.2–6.0 | 0.005–0.5:0.001–3.0 |
| L-AMPBs:glyphosate | 1:0.3–5.0 | 0.005–0.5:0.0015–2.5 |
| L-AMPBs:DPX-1108 | 1:0.5–20.0 | 0.005–0.5:0.025–10.0 |
| L-AMPBs:NP-48 | 1:0.5–15.0 | 0.005–0.5:0.0025–7.5 |
| L-AMPBs:linuron | 1:0.5–15.0 | 0.005–0.5:0.0025–7.5 |
| L-AMPBS:ATA | 1:0.3–10.0 | 0.005–0.5:0.0015–5.0 |
| L-AMPBs:cholines | 1:0.5–5 | 0.005–0.5:0.0025–2.5 |
| L-AMPBs:diethylamines | 1:0.3–3 | 0.005–0.5:0.0015–1.5 |

*molar ratio
NP-48: 2-(1-allyloxyamino butylidene)-5,5-dimethyl-4-methoxycarbonylcyclohexane-1,3-dione
SL-501: α-[4-(3,5-dichloropyridyl-2-hydroxy)phenoxy]-propionic acid
Dowco-233: 3,5,6-trichloro-2-pyridyloxyacetic acid
linuron: 3-(3,4-dichlorophenyl)-1-methoxy-1-methylurea
MCP: 2-methyl-4-chlorophenoxyacetic acid
3,4-DP: α-(3,4-dichlorophenoxy)propionic acid
MCPP: 2-(2-methyl-4-chlorophenoxy)propionic acid
MCPB: γ-(2-methyl-4-chlorophenoxy)butyric acid
2,4,5-T: 2-(2,4,5-trichlorophenoxy)propionic acid
2,3,6-TBA: 2,3,6-trichlorobenzoic acid
Banvel-D: 3,6-dichloro-2-methoxybenzoic acid
amiben: 3-amino-2,5-dichlorobenzoic acid
TPA: 2,3,6-trichlorophenylacetic acid
ATA: 3-amino-1,2,4-triazole AMPBs or L-AMPBs, or mixtures thereof with above mentioned herbicides or synergists may be formulated into water-soluble powder, liquid formulation, wettable powder, emulsion, dust or granules, with appropriate diluents. The formulations may contain surfactants such as polyoxyethylene octylphenyl ether, polyoxyethylene dodecyl ether, polyoxyethylene fatty acid ester and polyoxyethylene alkylaryl ether to improve spreading, adhesion and dispersion and to enable certain and enhanced effects.

The following are examples of formulation, to which the scope of the invention may not be restricted:

FORMULATION 1

Liquid formulation 30.0% by weight of monosodium salt of AMPB, 15.0% of polyoxyethylene octylphenyl ether, 0.15% of mehtyl p-hydroxybenzoate and 54.85% of water are mixed and dissolved to make the formulation. Upon application, it is diluted with water and subjected to foliar treatment.

FORMULATION 2

Wettable Powder 50.0% of monosodum salt of L-AMPB, 45.0% of diatomaceous earth and 5.0% of nonionic/anionic surfactant are finely pulverized and mixed homogeneously to make the formulation.

Upon application, it is diluted with water and subjected to foliar treatment.

FORMULATION 3

Dust 5.0% of monoisopropylamine salt of AMPB, 10.0% of CMH and 85.0% of talc are pulverized and blended homogeneously to make the formulation. Upon application, it is subjected to foliar treatment, as such, in amount of 0.4–6 kg. per 10 are.

FORMULATION 4

Liquid Formulation 10.0% of monosodium salt of L-AMPB, 20.0% of CMH, 15.0% of polyoxyethylene octylphenyl ether, 0.15% of methyl p-hydroxybenzoate and 54.85% of water are thoroughly mixed and dissolved to make the formualation. Upon application, it is diluted with water and subjected to foliar treatment.

The following are examples of the invention.

EXAMPLE 1

Salts of DL-AMPB or L-AMPB, or mixtures thereof with CMH were diluted to concentrations indicated in Table 2 and sprayed by foliar application to bitter dock transplanted to pots of diameter of 20 cm. in amount of 100 liter per 10 are.

Killing index of upperground part after 21 days (0: no effect, 5: death), as well as killing index and reproduction-inhibiting effect at underground part after 4 months (−: no reproduction, +++: maximum reproduction) were determined.

The detail of this assessment made in this Example was as follows:

| Killing index | Foiliage Damage (%) |
| --- | --- |
| 0 | 0 |
| 1 | 20% |
| 2 | 40% |
| 3 | 60% |
| 4 | 80% |
| 5 | 100% |

Four months after treatment, evaluation was made for inhibition of reproduction expressed in terms of symbols ranging from (−) to (+++) where (−) means no reproduction, namely complete suppression of reproduction, (±) remarkable suppression of reproduction; (+) considerable suppression of reproduction;

(++) medium suppression of reproduction; and (+++) no suppression of reproduction.

As the surfactant, 0.1% of polyoxyethylene octylphenyl ether was added to each spraying solution. The results are shown in Table 2.

TABLE 2

| | After 21 days | | After 4 months | | | |
|---|---|---|---|---|---|---|
| | AMPB concentration (wt. %) | | | | | |
| | 0.025 | 0.05 | 0.025 | | 0.05 | |
| DL-AMPB Na salt | 0 | 2 | 0 | +++ | 0 | +++ |
| DL-AMPB di-Na salt | 0 | 2 | 0 | +++ | 0 | +++ |
| DL-AMPB K salt | 0 | 2 | 0 | +++ | 0 | +++ |
| DL-AMPB di-K salt | 0 | 2 | 0 | +++ | 0 | +++ |
| DL-AMPB i-PrNH$_2$ salt | 1 | 2.5 | 0 | +++ | 0 | +++ |
| DL-AMPB n-BuNH$_2$ salt | 1 | 2.5 | 0 | +++ | 0 | +++ |
| L-AMPB Na salt | 2 | 3 | 0 | +++ | 2 | ++ |
| L-AMPB di-Na salt | 2 | 3 | 0 | +++ | 2 | + |
| L-AMPB L salt | 2 | 3 | 0 | +++ | 2 | ++ |
| L-AMPB di-K salt | 2 | 3 | 0 | +++ | 2 | ++ |
| L-AMPB i-PrNH$_2$ salt | 2.5 | 3.5 | 0 | +++ | 2.5 | + |
| L-AMPB n-BuNH$_2$ salt | 2.5 | 3.5 | 0 | +++ | 2.5 | ++ |
| CMH (0.3%) | | 1 | | 0 | | +++ |
| DL-AMPB Na + CMH (0.3%) | 2 | 3.5 | 1 | +++ | 4 | ± |
| DL-AMPB di-Na + CMH (0.3%) | 2 | 3.5 | 1 | +++ | 4 | ± |
| DL-AMPB K + CMH (0.3%) | 2 | 3.5 | 1 | +++ | 4 | ± |
| DL-AMPB di-K + CMH (0.3%) | 2 | 3.5 | 1 | +++ | 4 | ± |
| DL-AMPB i-PrNH$_2$ + CMH (0.3%) | 2.5 | 4 | 1.5 | +++ | 4.5 | ± |
| DLAMPB n-BuNH$_2$ + CMH (0.3%) | 2.5 | 4 | 1.5 | +++ | 4.5 | ± |
| L-AMPB Na + CMH (0.3%) | 3.5 | 4.5 | 4 | ± | 5 | — |
| L-AMPB di-Na + CMH (0.3%) | 3.5 | 4.5 | 4 | ± | 5 | — |
| L-AMPB K + CMH (0.3%) | 3.5 | 4.5 | 4 | ± | 5 | — |
| L-AMPB di-K + CMH (0.3%) | 3.5 | 4.5 | 4 | ± | 5 | — |
| L-AMPB i-PrNH$_2$ + CMH (0.3%) | 4 | 5 | 4.5 | ± | 5 | — |
| L-AMPB n-BuNH$_2$ + CMH (0.3%) | 4 | 5 | 4.5 | ± | 5 | — |
| None | | 0 | | 0 | | +++ |

As shown in Table 2, 0.05% of DL-AMPB alone killed upperground part after 21 days considerably, while 0.05% of L-AMPB alone not only killed upperground part after 21 days and 4 months considerably but also inhibited the reproduction to some extent. The mixtures of L-AMPB with CMH exhibited about twice killing and reproduction-inhibiting effects as compared with the mixtures of DL-AMPB with CMH. In comparison of the mixtures of L-AMPB with CMH against L-AMPB alone, 0.025% of L-AMPB killed 40-50% of bitter dock after 21 days but failed to inhibit the reproduction. 0.3% of CMH showed neither killing effect nor reproduction-inhibiting effect. Whereas, the mixtures of 0.025% of L-AMPB with 0.3% of CMH killed 80-90% of bitter dock after 4 months, yellowed the remaining leaves and deprived them of the activity, finally leading to death and inhibition of reproduction. As mentioned above, the effects of the mixtures of L-AMPB with CMH were more remarkable than the mixtures of DL-AMPB with CMH, which however, could be used sufficiently for the practical control of bitter dock.

EXAMPLE 2

Sodium salts of DL-AMPB or L-AMPB, or glyhosate were sprayed by foliar application to naturally growing perennial weeds in amount of 150 liter per 10 are. As the surfactant, 0.1% of polyoxyethylene octylphenyl ether was added to each spraying solution. Killing index and reproduction-inhibiting effect was determined after 21 days and 4 months, respectively, in accordance with the same evaluation standards as in Example 1. The heights or lengths of weeds were 100 cm. for azumanezasa, 50 cm. for wormwood, 30 cm. for bitter dock, 20-30 cm. for yabugarashi (*Cayratia japonica* Houtt.), about 70 cm. for needle grass (*Imperata cylindrica* Beauv.), about 5 m. for kudzu (*Pueraria thunbergiana* Benth.), 40 cm. for inuwarabi (*Athyrium niponicum* Hance), 40-50 cm. for warunasubi (*Solanum carolinense* L.) and 15 cm. for hedge bindweed, respectively.

The weeds were all several years old after germination. The results are shown in Table 3.

TABLE 3

| Concentration (%) (g./10 are) | | After 21 days | | | | | | | | | |
|---|---|---|---|---|---|---|---|---|---|---|---|
| | | A | B | C | D | E | F | G | H | I | J |
| DL-AMPB Na salt | 0.05 (75) | 1 | 2 | 2 | 1 | 2 | 1 | 1 | 2 | 0 | 2 |
| | 0.1 (150) | 3 | 4 | 3 | 3 | 4 | 3 | 2 | 4 | 1 | 5 |
| | 0.2 (300) | 5 | 5 | 5 | 5 | 5 | 5 | 3 | 5 | 3 | 5 |
| L-AMPB Na salt | 0.05 (75) | 2.5 | 4 | 3 | 3 | 3 | 3 | 3 | 3 | 1 | 3 |
| | 0.1 (150) | 4.5 | 5 | 5 | 5 | 5 | 4.5 | 4 | 5 | 3 | 5 |
| | 0.2 (300) | 5 | 5 | 5 | 5 | 5 | 5 | 5 | 5 | 5 | 5 |
| glyphosate isopropyl-amino salt | 0.05 (75) | 0 | 0 | 0 | 0 | 0 | 1 | 0 | 1 | 0 | 1 |
| | 0.1 (150) | 1 | 1 | 1 | 1 | 1 | 3 | 2 | 3 | 2 | 2 |
| | 0.2 (300) | 3 | 4 | 3 | 2 | 4 | 5 | 3 | 4 | 4 | 4 |
| None | | 0 | 0 | 0 | 0 | 0 | 0 | 0 | 0 | 0 | 0 |
| Concentration (%) (g./10 are) | | After 4 months | | | | | | | | | |
| | | A | B | C | D | E | F | G | H | I | J |
| | 0.05 (75) | +++ | ++ | ++ | +++ | ++ | +++ | +++ | +++ | +++ | +++ |

TABLE 3-continued

| | | | A | B | C | D | E | F | G | H | I | J |
|---|---|---|---|---|---|---|---|---|---|---|---|---|
| DL-AMPB Na salt | 0.1 | (150) | + | + | ++ | +++ | ++ | ++ | ++ | +++ | +++ | +++ |
| | 0.2 | (300) | − | − | − | ++ | − | − | − | + | + | ++ |
| | 0.05 | (75) | ++ | + | + | ++ | ++ | ++ | ++ | +++ | +++ | +++ |
| L-AMPB Na salt | 0.1 | (150) | − | − | − | + | − | − | − | + | + | ++ |
| | 0.2 | (300) | − | − | − | ± | − | − | − | ± | − | + |
| | 0.05 | (75) | +++ | +++ | +++ | +++ | +++ | +++ | +++ | +++ | +++ | +++ |
| glyphosate isopropyl-amino salt | 0.1 | (150) | ++ | ++ | ++ | +++ | ++ | ++ | ++ | +++ | +++ | ++ |
| | 0.2 | (300) | + | + | + | ++ | ± | + | + | + | + | +++ |
| None | | | +++ | +++ | +++ | +++ | +++ | +++ | +++ | +++ | +++ | +++ |

A: azumanezasa
B: wormwood
C: bitter dock
D: yabugarashi
E: needle grass
F: kudzu
G: inuwarabi
H: warunasubi
I: purple nutsedge
J: hedge bindweed

EXAMPLE 3.

Naturally growing bitter dock which is several years old after germination and noshiba which is a perennial, gramineous weed were transplanted to pots. After taking of roots, each spraying solution indicated in Table 4 was sprayed by foliar application in amount of 100 liter per 10 are. Killing index after 21 days and reproduction-inhibiting effect after 3 months were determined in accordance with the same evaluation standard as in Example 1, and the results are shown in Table 4. In the Table, A means the sodium salt of DL-AMPB and LA means the sodium salt of L-AMPB.

TABLE 4

| | | After 21 days | | After 3 months | |
|---|---|---|---|---|---|
| | Concentration (%) | bitter dock | noshiba | bitter dock | noshiba |
| | A 0.05 | 2 | 1.5 | +++ | +++ |
| | A 0.1 | 3.5 | 2.5 | ++ | ++ |
| 2,4-D Na salt | 0.1 | 1 | 0 | +++ | +++ |
| 2,4-D Na salt | 0.2 | 2 | 0 | +++ | +++ |
| 2,4-D Na salt | 0.1 + A 0.05 | 5 | 3.5 | ++ | ++ |
| 2,4-D Na salt | 0.1 + A 0.1 | 5 | 4 | + | + |
| 2,4-D Na salt | 0.2 + A 0.05 | 5 | 4.5 | − | − |
| 2,4-D Na salt | 0.2 + A 0.1 | 5 | 4.5 | − | − |
| CMH | 0.3 | 0 | 0 | +++ | +* |
| CMH | 0.6 | 0 | 0 | +++ | +* |
| CMH | 0.3 + A 0.05 | 4.5 | 3.5 | − | − |
| CMH | 0.3 + A 0.1 | 4.5 | 4 | − | − |
| CMH | 0.6 + A 0.05 | 5 | 5 | − | − |
| CMH | 0.6 + A 0.1 | 5 | 5 | − | − |
| DPX-1108 ammonium salt | 0.15 | 0 | 0 | +++ | ++* |
| DPX-1108 ammonium salt | 0.3 | 0 | 0 | +++ | +* |
| DPX-1108 ammonium salt | 0.15 + A 0.05 | 1 | 2 | ++ | + |
| DPX-1108 ammonium salt | 0.15 + A 0.1 | 1 | 2.5 | + | + |
| DPX-1108 ammonium salt | 0.3 + A 0.05 | 4 | 4 | − | − |
| DPX-1108 ammonium salt | 0.3 + A 0.1 | 4 | 4.5 | − | − |
| SL-501 Na salt | 0.15 | 1 | 2 | +++ | ++ |
| SL-501 Na salt | 0.3 | 1 | 3 | +++ | ++ |
| SL-501 Na salt | 0.15 + A 0.05 | 2 | 4 | ++ | + |
| SL-501 Na salt | 0.15 + A 0.1 | 2 | 4.5 | ++ | + |
| SL-501 Na salt | 0.3 + A 0.05 | 3 | 4.5 | ± | − |
| SL-501 Na salt | 0.3 + A 0.1 | 3 | 5 | ± | − |
| Dowco-233 triethylamine salt | 0.05 | 3 | 0 | + | +++ |
| Dowco-233 triethylamine salt | 0.1 | 4 | 0 | + | +++ |
| Dowco-233 triethylamine salt | 0.05 + A 0.05 | 5 | 2.5 | + | + |
| Dowco-233 triethylamine salt | 0.05 + A 0.1 | 5 | 3 | + | + |
| Dowco-233 triethylamine salt | 0.1 + A 0.05 | 5 | 5 | − | − |
| Dowco-233 triethylamine salt | 0.1 + A 0.1 | 5 | 5 | − | − |
| NP-48 | 0.15 | 1 | 2 | +++ | ++ |
| NP-48 | 0.3 | 1 | 3.5 | +++ | ++ |
| NP-48 | 0.15 + A 0.05 | 2 | 4 | +++ | + |
| NP-48 | 0.15 + A 0.1 | 2 | 4 | ++ | + |
| NP-48 | 0.3 + A 0.05 | 3 | 4.5 | ± | − |
| NP-48 | 0.3 + A 0.1 | 3 | 5 | ± | − |
| linuron | 0.1 | 4 | 2 | +++ | +++ |
| linuron | 0.3 | 4 | 5 | +++ | +++ |
| linuron | 0.1 + A 0.05 | 5 | 3 | ++ | + |
| linuron | 0.1 + A 0.1 | 5 | 5 | ++ | + |
| linuron | 0.3 + A 0.05 | 5 | 4 | − | − |
| linuron | 0.3 + A 0.1 | 5 | 5 | − | − |
| glyphosate isopropyl-amine salt | 0.05 | 1.5 | 1 | +++ | +++ |
| glyphosate isopropyl-amine salt | 0.1 | 2.5 | 2 | ++ | ++ |
| glyphosate isopropyl-amine salt | 0.05 + A 0.05 | 4 | 3.5 | + | + |
| glyphosate isopropyl-amine salt | 0.05 + A 0.1 | 5 | 5 | − | − |
| glyphosate | 0.1 + A 0.05 | 5 | 4.5 | − | − |

TABLE 4-continued

| Concentration (%) | | After 21 days bitter dock | noshiba | After 3 months bitter dock | noshiba |
|---|---|---|---|---|---|
| isopropyl-amine salt glyphosate | 0.1 + A 0.1 | 5 | 5 | — | — |
| isopropyl-amine salt | | | | | |
| choline . HCl | 0.1 | 0 | 0 | +++ | +++ |
| choline . HCl | 0.2 | 0 | 0 | +++ | +++ |
| choline . HCl | 0.1 + A 0.05 | 3.5 | 3 | ± | ± |
| choline . HCl | 0.1 + A 0.1 | 4.5 | 4 | — | — |
| choline . HCl | 0.2 + A 0.05 | 5 | 5 | — | — |
| choline . HCl | 0.2 + A 0.1 | 5 | 5 | — | — |
| diethylamine . HCl | 0.1 | 0 | 0 | +++ | +++ |
| diethylamine . HCl | 0.2 | 0 | 0 | +++ | +++ |
| diethylamine . HCl | 0.1 + A 0.05 | 3 | 2.5 | ± | ± |
| diethylamine . HCl | 0.1 + A 0.1 | 4 | 4 | — | — |
| diethylamine . HCl | 0.2 + A 0.05 | 5 | 5 | — | — |
| diethylamine . HCl | 0.2 + A 0.1 | 5 | 5 | — | — |
|  | LA 0.025 | 2 | 1.5 | +++ | +++ |
|  | LA 0.05 | 3.5 | 2.5 | ++ | +++ |
| CMH | 0.3 | 0 | 0 | +++ | ++* |
| CMH | 0.6 | 0 | 0 | +++ | +* |
| CMH | 0.3 + LA 0.025 | 4.5 | 3.5 | — | — |
| CMH | 0.3 + LA 0.05 | 4.5 | 4 | — | — |
| CMH | 0.6 + LA 0.025 | 5 | 5 | — | — |
| CMH | 0.6 + LA 0.05 | 5 | 5 | — | — |
| 2,4-D Na salt | 0.1 | 1 | 0 | +++ | +++ |
| 2,4-D Na salt | 0.2 | 2 | 0 | +++ | ++* |
| 2,4-D Na salt | 0.1 + LA 0.025 | 5 | 3.5 | — | + |
| 2,4-D Na salt | 0.1 + LA 0.05 | 5 | 5 | — | — |
| 2,4-D Na salt | 0.2 + LA 0.025 | 5 | 5 | — | — |
| 2,4-D Na salt | 0.2 + LA 0.05 | 5 | 5 | — | — |
| MCP Na salt | 0.1 | 1 | 0 | +++ | +++ |
| MCP Na salt | 0.2 | 2 | 0 | +++ | +++ |
| MCP Na salt | 0.1 + LA 0.025 | 4.5 | 3 | + | + |
| MCP Na salt | 0.1 + LA 0.05 | 4.5 | 4 | — | — |
| MCP Na salt | 0.2 + LA 0.025 | 5 | 5 | — | — |
| MCP Na salt | 0.2 + LA 0.05 | 5 | 5 | — | — |
| 3,4-DP | 0.1 | 1 | 0 | +++ | +++ |
| 3,4-DP | 0.2 | 2 | 0 | +++ | +++ |
| 3,4-DP | 0.1 + LA 0.025 | 4 | 3 | + | + |
| 3,4-DP | 0.1 + LA 0.05 | 4 | 4.5 | — | — |
| 3,4-DP | 0.2 + LA 0.025 | 5 | 5 | — | — |
| 3,4-DP | 0.2 + LA 0.05 | 5 | 5 | — | — |
| MCPP Na salt | 0.1 | 1 | 0 | +++ | +++ |
| MCPP Na salt | 0.2 | 2 | 0 | +++ | +++ |
| MCPP Na salt | 0.1 + LA 0.025 | 4.5 | 3 | + | + |
| MCPP Na salt | 0.1 + LA 0.05 | 4.5 | 4 | — | — |
| MCPP Na salt | 0.2 + LA 0.025 | 5 | 5 | — | — |
| MCPP Na salt | 0.2 + LA 0.05 | 5 | 5 | — | — |
| MCPB Na Salt | 0.1 | 1 | 0 | +++ | +++ |
| MCPB Na salt | 0.2 | 2 | 0 | +++ | +++ |
| MCPB Na salt | 0.1 + LA 0.025 | 4.5 | 3 | + | + |
| MCPB Na salt | 0.1 + LA 0.05 | 4.5 | 4 | — | — |
| MCPB Na salt | 0.2 + LA 0.025 | 5 | 5 | — | — |
| MCPB Na salt | 0.2 + La 0.05 | 5 | 5 | — | — |
| 2,4,5-T Na salt | 0.1 | 1 | 0 | +++ | +++ |
| 2,4,5-T Na salt | 0.2 | 2 | 0 | +++ | +++ |
| 2,4,5-T Na salt | 0.1 + LA 0.025 | 4.5 | 4 | ± | ± |
| 2,4,5-T Na salt | 0.1 + LA 0.05 | 4.5 | 4 | — | — |
| 2,4,5-T Na salt | 0.2 + LA 0.025 | 5 | 5 | — | — |
| 2,4,5-T Na salt | 0.2 + LA 0.05 | 5 | 5 | — | — |
| SL-501 Na salt | 0.1 | 0.5 | 2 | +++ | ++ |
| SL-501 Na salt | 0.2 | 2 | 3 | +++ | ++ |
| SL-501 Na salt | 0.1 + LA 0.025 | 2.5 | 4 | ++ | — |
| SL-501 Na salt | 0.1 + LA 0.05 | 3.5 | 4.5 | ++ | — |
| SL-501 Na salt | 0.2 + LA 0.025 | 3.5 | 4.5 | ± | — |
| SL-501 Na salt | 0.2 + LA 0.05 | 4.5 | 5 | ± | — |
| 2,3,6-TBA Na salt | 0.1 | 1 | 0 | +++ | +++ |
| 2,3,6-TBA Na salt | 0.2 | 2 | 0 | +++ | +++ |
| 2,3,6-TBA Na salt | 0.1 + LA 0.025 | 4 | 3 | + | + |
| 2,3,6-TBA Na salt | 0.1 + LA 0.05 | 4 | 3 | — | — |
| 2,3,6-TBA Na salt | 0.2 + LA 0.025 | 5 | 5 | — | — |
| 2,3,6-TBA Na salt | 0.2 + LA 0.05 | 5 | 5 | — | — |
| Banvel-D dimethyl-amine | 0.1 | 1 | 0 | +++ | +++ |
| Banvel-D dimethyl-amine | 0.2 | 2 | 0 | +++ | +++ |
| Banvel-D dimethyl-amine | 0.1 + LA 0.025 | 4 | 3 | + | + |
| Banvel-D dimethyl-amine | 0.1 + LA 0.05 | 4 | 4 | — | — |
| Banvel-D dimethyl-amine | 0.2 + LA 0.025 | 5 | 5 | — | — |
| Banvel-D dimethyl-amine | 0.2 + LA 0.05 | 5 | 5 | — | — |
| Amiben Na salt | 0.1 | 1 | 0 | +++ | +++ |
| Amiben Na salt | 0.2 | 2 | 0 | +++ | +++ |
| Amiben Na salt | 0.1 + LA 0.025 | 4 | 3 | + | + |
| Amiben Na salt | 0.1 + LA 0.05 | 4 | 3 | — | — |
| Amiben Na salt | 0.2 + LA 0.025 | 5 | 5 | — | — |

TABLE 4-continued

| Concentration (%) | | After 21 days bitter dock | noshiba | After 3 months bitter dock | noshiba |
|---|---|---|---|---|---|
| Amiben Na salt | 0.2 + LA 0.05 | 5 | 5 | — | — |
| TPA Na salt | 0.1 | 1 | 0 | +++ | +++ |
| TPA Na salt | 0.2 | 2 | 0 | +++ | +++ |
| TPA Na salt | 0.1 + LA 0.025 | 4 | 3 | + | + |
| TPA Na salt | 0.1 + LA 0.05 | 4 | 3 | — | — |
| TPA Na salt | 0.2 + LA 0.025 | 5 | 5 | — | — |
| TPA Na salt | 0.2 + LA 0.05 | 5 | 5 | — | — |
| Dowco-233 triethylamine salt | 0.05 | 3 | 0 | + | +++ |
| Dowco-233 triethylamine salt | 0.1 | 4 | 0 | + | +++ |
| Dowco-233 triethylamine salt | 0.05 + LA 0.025 | 5 | 2.5 | ± | ± |
| Dowco-233 triethylamine salt | 0.05 + LA 0.05 | 5 | 3.5 | — | — |
| Dowco-233 triethylamine salt | 0.1 + LA 0.025 | 5 | 5 | — | — |
| Dowco-233 triethylamine salt | 0.1 + LA 0.05 | 5 | 5 | — | — |
| glyphosate isopropyl-amine salt | 0.05 | 1.5 | 1 | +++ | +++ |
| glyphosate isopropyl-amine salt | 0.1 | 2.5 | 2 | ++ | ++ |
| glyphosate isopropyl-amine salt | 0.05 + LA 0.025 | 4 | 3.5 | + | + |
| glyphosate isopropyl-amine salt | 0.05 + LA 0.05 | 5 | 5 | — | — |
| glyphosate isopropyl-amine salt | 0.1 + LA 0.025 | 5 | 4.5 | — | — |
| glyphosate isopropyl-amine salt | 0.1 + LA 0.05 | 5 | 5 | — | — |
| DPX-1108 ammonium salt | 0.2 | 0 | 0 | +++ | ++* |
| DPX-1108 ammonium salt | 0.4 | 0 | 0 | +++ | +* |
| DPX-1108 ammonium salt | 0.2 + LA 0.025 | 2 | 2.5 | + | + |
| DPX-1108 ammonium salt | 0.2 + LA 0.05 | 3 | 3.5 | — | — |
| DPX-1108 ammonium salt | 0.4 + LA 0.025 | 4.5 | 4.5 | — | — |
| DPX-1108 ammonium salt | 0.4 + LA 0.05 | 4.5 | 4.5 | — | — |
| NP-48 | 0.15 | 1 | 2 | +++ | ++ |
| NP-48 | 0.3 | 1 | 3.5 | +++ | ++ |
| NP-48 | 0.15 + LA 0.025 | 2.5 | 4 | ++ | — |
| NP-48 | 0.15 + LA 0.05 | 3 | 4.5 | + | — |
| NP-48 | 0.3 + LA 0.025 | 3.5 | 5 | ± | — |
| NP-48 | 0.3 + LA 0.05 | 4 | 5 | ± | — |
| linuron | 0.1 | 3 | 2 | +++ | +++ |
| linuron | 0.3 | 4 | 4 | +++ | +++ |
| linuron | 0.1 + LA 0.025 | 5 | 4 | ++ | + |
| linuron | 0.1 + LA 0.05 | 5 | 5 | — | — |
| linuron | 0.3 + LA 0.025 | 5 | 5 | — | — |
| linuron | 0.3 + LA 0.05 | 5 | 5 | — | — |
| ATA | 0.05 | 2 | 2 | +++ | +++ |
| ATA | 0.1 | 4 | 4 | +++ | +++ |
| ATA | 0.05 + LA 0.025 | 4 | 4 | ++ ++ ++ | ± |
| ATA | 0.05 + LA 0.05 | 5 | 5 | — | — |
| ATA | 0.1 + LA 0.025 | 5 | 5 | — | — |
| ATA | 0.1 + LA 0.05 | 5 | 5 | — | — |
| choline . HCl | 0.1 | 0 | 0 | +++ | +++ |
| choline . HCl | 0.2 | 0 | 0 | +++ | +++ |
| choline . HCl | 0.1 + LA 0.025 | 3.5 | 3 | ± | ± |
| choline . HCl | 0.1 + LA 0.05 | 4.5 | 4 | — | — |
| choline . HCl | 0.2 + LA 0.025 | 5 | 5 | — | — |
| choline . HCl | 0.2 + LA 0.05 | 5 | 5 | — | — |
| diethyl-amine . HCl | 0.1 | 0 | 0 | +++ | +++ |
| diethyl-amine . HCl | 0.2 | 0 | 0 | +++ | +++ |
| diethyl-amine . HCl | 0.1 + LA 0.025 | 3 | 2.5 | ± | ± |
| diethyl-amine . HCl | 0.1 + LA 0.05 | 4 | 4 | — | — |
| diethyl-amine . HCl | 0.2 + LA 0.025 | 5 | 5 | — | — |
| diethyl-amine . HCl | 0.2 + LA 0.05 | 5 | 5 | — | — |
| None | | 0 | 0 | +++ | +++ |

*suppression of elongation of upperground part.

EXAMPLE 4.

Sodium salt of DL-AMPB, L-AMPB, CMH or mixtures thereof were diluted and sprayed by foliar application to naturally growing perennial weeds in amount of 150 liter per 10 are.

Each spraying solution contained 0.1% of polyoxyehtylene octylphenyl ether as the surfactant. Killing index after 21 days and reproduction-inhibiting effect after 4 months were determined in accordance with the same evaluation standards as in Example 1 and the results are shown in Tables 5 and 6. In the Tables, symbols A, B, C, D, E, F, G, H, I and J have the same meanings as in Example 2.

TABLE 5

| Concentration (%) | After 21 days | | | | | | | | | |
|---|---|---|---|---|---|---|---|---|---|---|
| | A | B | C | D | E | F | G | H | I | J |
| DL-AMPB 0.05 | 2 | 4 | 3 | 3 | 4 | 3 | 1 | 3 | 1 | 5 |
| DL-AMPB 0.1 | 4 | 5 | 4 | 4 | 5 | 4.5 | 2 | 4 | 2 | 5 |
| DL-AMPB 0.2 | 5 | 5 | 5 | 5 | 5 | 5 | 3 | 5 | 3 | 5 |
| DL-AMPB 0.4 | 5 | 5 | 5 | 5 | 5 | 5 | 4.5 | 5 | 4.5 | 5 |
| CMH 0.3 | 0 | 1 | 0 | 0 | 0 | 0 | 0 | 0 | 0 | 1 |

TABLE 5-continued

| | | | | | | | | | | |
|---|---|---|---|---|---|---|---|---|---|---|
| CMH 0.6 | 2 | 2 | 0 | 1 | 1 | 1 | 0 | 1 | 0 | 3 |
| DL-AMPB 0.05 + CMH 0.3 | 3 | 5 | 4 | 3 | 4.5 | 3 | 1 | 3.5 | 1.5 | 5 |
| DL-AMPB 0.05 + CMH 0.6 | 4 | 5 | 4.5 | 4 | 5 | 5 | 1 | 3.5 | 1.5 | 5 |
| DL-AMPB 0.1 + CMH 0.3 | 4.5 | 5 | 5 | 4.5 | 5 | 5 | 4 | 4.5 | 4 | 5 |
| DL-AMPB 0.1 + CMH 0.6 | 5 | 5 | 5 | 5 | 5 | 5 | 4 | 4.5 | 4 | 5 |
| DL-AMPB 0.2 + CMH 0.3 | 5 | 5 | 5 | 5 | 5 | 5 | 5 | 5 | 5 | 5 |
| DL-AMPB 0.2 + CMH 0.6 | 5 | 5 | 5 | 5 | 5 | 5 | 5 | 5 | 5 | 5 |
| None | 0 | 0 | 0 | 0 | 0 | 0 | 0 | 0 | 0 | 0 |

| | After 4 months | | | | | | | | | |
|---|---|---|---|---|---|---|---|---|---|---|
| Concentration (%) | A | B | C | D | E | F | G | H | I | J |
| DL-AMPB 0.05 | ++ | + | ++ | +++ | + | ++ | + | +++ | +++ | +++ |
| DL-AMPB 0.1 | + | − | + | +++ | ± | + | − | ++ | +++ | +++ |
| DL-AMPB 0.2 | − | − | − | +++ | ± | ± | − | + | ++ | +++ |
| DL-AMPB 0.4 | − | − | − | ++ | − | − | − | + | ++ | ++ |
| CMH 0.3 | ++ | ++ | +++ | +++ | +++ | +++ | +++ | ++ | ++ | ++ |
| CMH 0.6 | + | + | +++ | +++ | +++ | ++ | +++ | ++ | ++ | ++ |
| DL-AMPB 0.05 + CMH 0.3 | + | − | − | ++ | ± | + | + | + | ++ | − |
| DL-AMPB 0.05 + CMH 0.6 | − | − | − | + | ± | ± | + | + | ++ | − |
| DL-AMPB 0.1 + CMH 0.3 | − | − | − | ± | − | − | − | − | ± | − |
| DL-AMPB 0.1 + CMH 0.6 | − | − | − | ± | − | − | − | − | ± | − |
| DL-AMPB 0.2 + CMH 0.3 | − | − | − | − | − | − | − | − | − | − |
| DL-AMPB 0.2 + CMH 0.6 | − | − | − | − | − | − | − | − | − | − |
| None | +++ | +++ | +++ | +++ | +++ | +++ | +++ | +++ | +++ | +++ |

TABLE 6

| | | After 21 days | | | | | | | | | |
|---|---|---|---|---|---|---|---|---|---|---|---|
| Concentration (%) | | A | B | C | D | E | F | G | H | I | J |
| L-AMPB | 0.025 | 2 | 4 | 3 | 3 | 4 | 3 | 1 | 3 | 1 | 5 |
| L-AMPB | 0.05 | 4 | 5 | 4 | 4 | 5 | 4.5 | 2 | 4 | 2 | 5 |
| L-AMPB | 0.1 | 5 | 5 | 5 | 5 | 5 | 5 | 3 | 5 | 3 | 5 |
| L-AMPB | 0.2 | 5 | 5 | 5 | 5 | 5 | 5 | 4.5 | 5 | 4.5 | 5 |
| CMH | 0.3 | 0 | 1 | 0 | 0 | 0 | 0 | 0 | 0 | 0 | 1 |
| CMH | 0.6 | 2 | 2 | 0 | 1 | 1 | 1 | 0 | 1 | 0 | 3 |
| L-AMP 0.025 + CMH | 0.3 | 3 | 5 | 4 | 3 | 4.5 | 4 | 3 | 4 | 2 | 5 |
| L-AMP 0.025 + CMH | 0.6 | 4 | 5 | 4.5 | 4 | 5 | 5 | 3 | 4 | 2 | 5 |
| L-AMP 0.05 + CMH | 0.3 | 4.5 | 5 | 5 | 4.5 | 5 | 5 | 4 | 5 | 4 | 5 |
| L-AMP 0.05 + CMH | 0.6 | 5 | 5 | 5 | 5 | 5 | 5 | 4 | 5 | 4.5 | 5 |
| L-AMP 0.1 + CMH | 0.3 | 5 | 5 | 5 | 5 | 5 | 5 | 5 | 5 | 5 | 5 |
| L-AMP 0.1 + CMH | 0.6 | 5 | 5 | 5 | 5 | 5 | 5 | 5 | 5 | 5 | 5 |
| None | | 0 | 0 | 0 | 0 | 0 | 0 | 0 | 0 | 0 | 0 |

| | | After 4 months | | | | | | | | | |
|---|---|---|---|---|---|---|---|---|---|---|---|
| Concentration (%) | | A | B | C | D | E | F | G | H | I | J |
| L-AMPB | 0.025 | ++ | + | ++ | +++ | + | ++ | + | +++ | +++ | +++ |
| L-AMPB | 0.05 | + | − | + | +++ | ± | + | − | ++ | +++ | +++ |
| L-AMPB | 0.1 | − | − | − | +++ | ± | ± | − | + | ++ | +++ |
| L-AMPB | 0.2 | − | − | − | ++ | − | − | − | + | ++ | ++ |
| CMH | 0.3 | ++ | ++ | +++ | +++ | +++ | +++ | +++ | ++ | ++ | ++ |
| CMH | 0.6 | + | + | +++ | +++ | +++ | ++ | ++ | ++ | ++ | ++ |
| L-AMP 0.025 + CMH | 0.3 | + | − | − | ++ | ± | + | + | + | ++ | − |
| L-AMP 0.025 + CMH | 0.6 | − | − | − | + | ± | ± | + | + | ++ | − |
| L-AMP 0.05 + CMH | 0.3 | − | − | − | ± | − | − | − | − | ± | − |
| L-AMP 0.05 + CMH | 0.6 | − | − | − | ± | − | − | − | − | − | − |
| L-AMP 0.1 + CMH | 0.3 | − | − | − | − | − | − | − | − | − | − |
| L-AMP 0.1 + CMH | 0.6 | − | − | − | − | − | − | − | − | − | − |
| None | | +++ | +++ | +++ | +++ | +++ | +++ | +++ | +++ | +++ | +++ |

As shown in Tables 5 and 6 the reproduction-inhibiting activity of AMPB was surprisingly enhanced and the weeding spectrum was broadened by mixing it with CMH.

EXAMPLE 5

Sodium salt of DL-AMPB, 1-AMPB, CMH or mixtures thereof were diluted and sprayed by foliar application in amount of 150 liter per 10 are on Japanese cypress forest land.

Killing index after 30 days and 3 months was determined in accordance with the same evaluation standard as in Example 1, and the results are shown in Tables 7 and 8.

TABLE 7

| | After 30 days | | | | | After 3 months | | | | |
|---|---|---|---|---|---|---|---|---|---|---|
| Concentration (%) | K | L | M | N | O | K | L | M | N | O |
| DL-AMPB 0.125 | 0 | 5 | 3 | 3 | 4 | 0 | 4 | 2 | 2 | 3 |
| DL-AMPB 0.25 | 0 | 5 | 4 | 4 | 4 | 0 | 5 | 3 | 3 | 4 |
| DL-AMPB 0.5 | 0 | 5 | 5 | 5 | 5 | 0 | 5 | 4.5 | 4.5 | 5 |
| CMH 0.25 | 0 | 0 | 0 | 0 | 0 | 0 | 0 | 0 | 0 | 0 |
| CMH 0.5 | 0 | 1 | 1 | 1 | 1 | 0 | 0 | 1 | 0 | 1 |
| CMH 1.0 | 0 | 3 | 3 | 2 | 2 | 0 | 1 | 2 | 1 | 2 |
| DL-AMPB 0.125 + CMH 0.25 | 0 | 5 | 3 | 3.5 | 4 | 0 | 5 | 4.5 | 4 | 4.5 |
| DL-AMPB 0.125 + CMH 0.5 | 0 | 5 | 4 | 4 | 4.5 | 0 | 5 | 5 | 4.5 | 5 |
| DL-AMPB 0.125 + CMH 1.0 | 0 | 5 | 4 | 4 | 4.5 | 0 | 5 | 5 | 5 | 5 |
| DL-AMPB 0.25 + CMH 0.25 | 0 | 5 | 4.5 | 4.5 | 4 | 0 | 5 | 5 | 4.5 | 5 |
| DL-AMPB 0.25 + | 0 | 5 | 5 | 5 | 5 | 0 | 5 | 5 | 5 | 5 |

TABLE 7-continued

| Concentration (%) | After 30 days | | | | | After 3 months | | | | |
|---|---|---|---|---|---|---|---|---|---|---|
| | K | L | M | N | O | K | L | M | N | O |
| CMH 0.5 | | | | | | | | | | |
| DL-AMPB 0.25 + CMH 1.0 | 0 | 5 | 5 | 5 | 5 | 0 | 5 | 5 | 5 | 5 |
| DL-AMPB 0.5 + CMH 0.25 | 0 | 5 | 5 | 5 | 5 | 0 | 5 | 5 | 5 | 5 |
| DL-AMPB 0.5 + CMH 0.5 | 0 | 5 | 5 | 5 | 5 | 0 | 5 | 5 | 5 | 5 |
| DL-AMPB 0.5 + CMH 1.0 | 0 | 5 | 5 | 5 | 5 | 0 | 5 | 5 | 5 | 5 |
| None | 0 | 0 | 0 | 0 | 0 | 0 | 0 | 0 | 0 | 0 |

TABLE 8

| Concentration (%) | After 30 days | | | | | After 3 months | | | | |
|---|---|---|---|---|---|---|---|---|---|---|
| | K | L | M | N | O | K | L | M | N | O |
| L-AMPB 0.063 | 0 | 5 | 3 | 3 | 4 | 0 | 4 | 2 | 2 | 3 |
| L-AMPB 0.125 | 0 | 5 | 4 | 4 | 4 | 0 | 5 | 3 | 3 | 4 |
| L-AMPB 0.25 | 0 | 5 | 5 | 5 | 5 | 0 | 5 | 4.5 | 4.5 | 5 |
| CMH 0.25 | 0 | 0 | 0 | 0 | 0 | 0 | 0 | 0 | 0 | 0 |
| CMH 0.5 | 0 | 1 | 1 | 1 | 1 | 0 | 0 | 1 | 0 | 1 |
| CMH 1.0 | 0 | 3 | 3 | 2 | 2 | 0 | 1 | 2 | 1 | 2 |
| L-AMPB 0.63 + CMH 0.25 | 0 | 5 | 3 | 3.5 | 4 | 0 | 5 | 4.5 | 4 | 4.5 |
| L-AMPB 0.63 + CMH 0.5 | 0 | 5 | 4 | 4 | 4.5 | 0 | 5 | 5 | 4.5 | 5 |
| L-AMPB 0.63 + CMH 1.0 | 0 | 5 | 4 | 4 | 4.5 | 0 | 5 | 5 | 5 | 5 |
| L-AMPB 0.125 + CMH 0.25 | 0 | 5 | 4.5 | 4.5 | 4 | 0 | 5 | 5 | 4.5 | 5 |
| L-AMPB 0.125 + CMH 0.5 | 0 | 5 | 5 | 5 | 5 | 0 | 5 | 5 | 5 | 5 |
| L-AMPB 0.125 + CMH 1.0 | 0 | 5 | 5 | 5 | 5 | 0 | 5 | 5 | 5 | 5 |
| L-AMPB 0.25 + CMH 0.25 | 0 | 5 | 5 | 5 | 5 | 0 | 5 | 5 | 5 | 5 |
| L-AMPB 0.25 + CMH 0.5 | 0 | 5 | 5 | 5 | 5 | 0 | 5 | 5 | 5 | 5 |
| L-AMPB 0.25 + CMH 1.0 | 0 | 5 | 5 | 5 | 5 | 0 | 5 | 5 | 5 | 5 |
| None | 0 | 0 | 0 | 0 | 0 | 0 | 0 | 0 | 0 | 0 |

K: Japanese cypress
L: chestnut
M: miyakozasa
N: eulalia
O: kumaichigo

EXAMPLE 6

Sodium salts of DL-AMPB or L-AMPB, or glyphosate were sprayed by foliar application in amount of 150 liter per 10 are at a naturally growing brush. Each spraying solution contained 0.1% of polyoxyethylene octylphenyl ether as the surfactant. Killing index after 1 month and 3 months as well as reproductioninhibiting effect after 3 months were determined in the same evaluation standards as in Example 1, and the results are shown in Table 9.

TABLE 9

| Concentration (%) (g./10 are) | | After 1 month | | | | | | | After 3 months Killing index | | | | | |
|---|---|---|---|---|---|---|---|---|---|---|---|---|---|---|
| | | P | Q | R | S | T | U | V | P | Q | R | S | T | U | V |
| DL-AMPB | 0.05 (75) | 0 | 1 | 1 | 1 | 1 | 1 | 1 | 0 | 0 | 0 | 0 | 0 | 0 | 0 |
| | 0.1 (150) | 1 | 3 | 3 | 3 | 3 | 3 | 3 | 1 | 1 | 1 | 1 | 1 | 1 | 1 |
| | 0.2 (300) | 3 | 5 | 5 | 5 | 4 | 5 | 5 | 2 | 5 | 5 | 5 | 5 | 5 | 5 |
| L-AMPB | 0.05 (75) | 2 | 3.5 | 4 | 3.5 | 3 | 3 | 3 | 1 | 1.5 | 1 | 2 | 1.5 | 1 | 1 |
| | 0.1 (150) | 4 | 5 | 5 | 5 | 4 | 5 | 5 | 3 | 5 | 4 | 5 | 5 | 5 | 5 |
| | 0.2 (300) | 5 | 5 | 5 | 5 | 5 | 5 | 5 | 4 | 5 | 5 | 5 | 5 | 5 | 5 |
| glyphosate isopropylamine salt | 0.05 (75) | 0 | 0 | 0 | 0 | 0 | 0 | 0 | 0 | 0 | 0 | 0 | 0 | 0 | 0 |
| | 0.1 (150) | 0 | 1 | 0 | 0 | 1 | 1 | 1 | 0 | 0 | 0 | 0 | 0 | 0 | 0 |
| | 0.2 (300) | 1.5 | 2 | 0 | 1 | 2 | 2 | 2 | 1 | 1 | 0 | 0 | 1 | 0 | 0 |
| None | | 0 | 0 | 0 | 0 | 0 | 0 | 0 | 0 | 0 | 0 | 0 | 0 | 0 | 0 |

| Concentration (%) (g./10 are) | | After 3 months Reproduction-inhibiting effect | | | | | | |
|---|---|---|---|---|---|---|---|---|
| | | P | Q | R | S | T | U | V |
| DL-AMPB | 0.05 (75) | +++ | +++ | +++ | +++ | +++ | +++ | +++ |
| | 0.1 (150) | ++ | +++ | ++ | ++ | ++ | ++ | ++ |
| | 0.2 (300) | ++ | − | − | − | − | − | − |
| L-AMPB | 0.05 (75) | +++ | ++ | +++ | ++ | ++ | +++ | ++ |
| | 0.1 (150) | ++ | − | + | − | − | − | − |
| | 0.2 (300) | ± | − | − | − | − | − | − |
| glyphosate isopropylamine salt | 0.05 (75) | +++ | +++ | +++ | +++ | +++ | +++ | +++ |
| | 0.1 (150) | +++ | +++ | +++ | +++ | +++ | +++ | +++ |
| | 0.2 (300) | ++ | ++ | +++ | +++ | ++ | +++ | +++ |
| None | | +++ | +++ | +++ | +++ | +++ | +++ | +++ |

P: Japanese bush cranberry
Q: kiichigo (*Rubus palmatus Thunb. forma coptophyllus Makino*)
R: Japanese prickly ash (*Xanthoxylum piperitum DC.*)
S: lace shrub (*Stephanandra incisa Zabel*)
T: yamazakura (*Prunus donarium Sieb. var. spontanae Makino*)
U: torch azalea
V: oak

EXAMPLE 7

Sodium salt of DL-AMPB or CMH, or mixtures thereof were sprayed by foliar application to shrubs of about 60–70 cm. height indicated in Table 8. Each spraying solution contained 0.1% of polyoxyethylene octylphenyl ether as the surfactant. Killing index after 21 days and reproduction-inhibiting effect after 4 months were determined in accordance with the same evaluation standards as in Example 1, and the results are shown in Table 10.

TABLE 10

| Concentration (%) | | After 21 days | | | | | After 4 months | | | | |
|---|---|---|---|---|---|---|---|---|---|---|---|
| | | W | X | Y | Z | L | W | X | Y | Z | L |
| DL-AMPB | 0.1 | 4 | 4 | 0 | 1 | 4 | + | + | +++ | +++ | + |
| DL-AMPB | 0.2 | 5 | 5 | 0 | 2 | 5 | − | − | +++ | + | − |
| DL-AMPB | 0.4 | 5 | 5 | 0 | 4 | 5 | − | − | +++ | ± | − |
| CMH | 0.3 | 0 | 0 | 0 | 0 | 0 | ++ | ++ | +++ | + | + |
| CMH | 0.6 | 0 | 0 | 0 | 0 | 0 | + | + | +++ | − | − |
| DL-AMPB 0.1 + CMH | 0.3 | 5 | 5 | 0 | 2 | 5 | − | − | +++ | ± | − |
| DL-AMPB 0.1 + CMH | 0.6 | 5 | 5 | 0 | 2 | 5 | − | − | +++ | − | − |
| DL-AMPB 0.2 + CMH | 0.3 | 5 | 5 | 0 | 3 | 5 | − | − | +++ | − | − |
| DL-AMPB 0.2 + CMH | 0.6 | 5 | 5 | 0 | 3 | 5 | − | − | +++ | − | − |
| DL-AMPB 0.4 + CMH | 0.3 | 5 | 5 | 0 | 4.5 | 5 | − | − | +++ | − | − |
| DL-AMPB 0.4 + CMH | 0.6 | 5 | 5 | 0 | 4.5 | 5 | − | − | +++ | − | − |
| None | 0 | 0 | 0 | 0 | 0 | 0 | +++ | +++ | +++ | +++ | +++ |

W: Japanese red pine (*Pinus densiflora* Sieb. et. Zucc. )
X: Japanese larch (*Larix leptolepis* Murray )
Y: Japanese cypress
Z: Japanese cedar
L: chestnut

EXAMPLE 8

Sodium salt of DL-AMPB, L-AMPB, CMH, or mixtures thereof were sprayed by foliar application to naturally growing shrubs on October 25, in amount of 150 liter per 10 are.

Each test area was 4 m² and each spraying solution contained 0.1% of polyoxyethylene octylphenyl ether as the surfactant. The reproduction-inhibiting effect was determined on May 23 of the next year in accordance with the same evaluation standard as in Example 1. The results are shown in Tables 12 and 13.

TABLE 12

| Concentration (%) | Reproduction-inhibiting effect | Remarks |
|---|---|---|
| DL-AMPB Na 0.125 | 3.5 | A' = 5, B' = 3, U = 5, A = 4.5 |
| DL-AMPB Na 0.25 | 4 | C' = 5, D' = 4.5, B' = 3.5 |
| DL-AMPB Na 0.5 | 5 | A' = 5, D' = 5, U = 5 |
| CMH 0.5 | 0.5–1 | D' = 0.5, U = 1.5–2, E' = 1.5 |
| CMH 1.0 | 1 | C' = 3.5–4, U = 3.5–4, D' = 0.5, others = slightly inhibited |
| CMH 2.0 | 1–1.5 | L = 3.5, D' = 1, F' = 1, others = slightly inhibited |
| DL-AMPB Na 0.125 + CMH 0.5 | 4.5 | almost not reproduced incl. of G' and E', A = 4.5–5 |
| DL-AMPB Na 0.125 + CMH 1.0 | 4.5 | H', U and A = almost not reproduced |
| DL-AMPB Na 0.125 + CMH 2.0 | 5 | A, B', A', L' and others = inhibited |

TABLE 13

| Concentration (%) | Reproduction-inhibiting effect | Remarks |
|---|---|---|
| L-AMPB Na 0.0625 | 3.5 | A' = 5, B' = 3, U = 5, A = 4.5 |
| L-AMPB 0.125 | 4 | C' = 5, D' = 4.5, B = 3.5 |
| L-AMPB 0.25 | 5 | A' = 5, D' = 5, U = 5 |
| CMH 0.5 | 0.5–1 | D' = 0.5, U = 1.5–2, E' = 1.5 |
| CMH 1.0 | 1 | C' = 3.5–4, U = 3.5–4, D' = 0.5, others = slightly inhibited |
| CMH 2.0 | 1–1.5 | L = 3.5, D' = 1, F' = 1, others = slightly inhibited |
| L-AMPB Na 0.0625 + CMH 0.5 | 4.5 | almost not reproduced incl. of G' and E', A = 4.5–5 |
| L-AMPB Na 0.0625 + CMH 1.0 | 4.5 | H', U and A = almost not reproduced |
| L-AMPB Na 0.0625 + CMH 2.0 | 5 | A, B', A', L' and others = inhibited |
| L-AMPB Na 0.125 + CMH 0.5 | 4.5 | D', U, A and B' = almost not reproduced |
| L-AMPB Na 0.125 + CMH 1.0 | 4.5 | B', U, D' = almost not reproduced |
| L-AMPB Na 0.125 + CMH 2.0 | 5 | not reproduced |
| L-AMPB Na 0.25 + CMH 0.5 | 5 | H' = slightly resistant others = not reproduced |
| L-AMPB Na 0.25 + CMH 1.0 | 5 | not reproduced |

TABLE 13-continued

| Concentration (%) | Reproduction-inhibiting effect | Remarks |
|---|---|---|
| L-AMPB Na 0.25 + CMH 2.0 | 5 | not reproduced |
| None | 0 | A' = 30 cm., |
|  |  | H' = 20 cm., |
|  |  | D' = 50 cm., |
|  |  | A = 75 cm., |
|  |  | U = 10-20 cm., |
|  |  | B' = 25 cm. |
| DL-AMPB Na 0.25 + CMH 0.5 | 4.5 | D', U, A and B' = almost not reproduced |
| DL-AMPB Na 0.25 + CMH 1.0 | 4.5 | B', U, D' = almost not reproduced |
| DL-AMPB Na 0.25 + CMH 2.0 | 5 | not reproduced |
| DL-AMPB Na 0.5 + CMH 0.5 | 5 | H' = slightly resistant others = not reproduced |
| DL-AMPB Na 0.5 + CMH 1.0 | 5 | not reproduced |
| DL-AMPB Na 0.5 + CMH 2.0 | 5 | not reproduced |
| None | 0 | A' = 30 cm., |
|  |  | H' = 20 cm., |
|  |  | D' = 50 cm., |
|  |  | A = 75 cm., |
|  |  | U = 10-20 cm., |
|  |  | B' = 25 cm. |

A': koajisai (*Hydrangea hirta* Sieb. et Zucc.)
B': toneriko (*Fraxinus japonica* Blume)
C': mizunara (*Quercus crispula* Blume)
D': tree clethra (*Clethra barbinervis* Sieb. et. Zucc.)
E': Japanese witch hazel (*Hamamemis japonica* Sieb. et. Zucc.)
F': yamaurushi (*Rhus trichocarpa* Miq.)
G': Japanese snowbell (*Styrax japonica* Sieb. et. Zucc.)
H': nejiki (Lyonia Neziki Nakai et Hara)
L': painted maple (*Acer mono* Maxim.)
A, L and U: same meanings as in Examples 2, 5 and 6.

EXAMPLE 9

In order to evaluate the effects of AMPBs against evergreen shrubs, sodium salt of L-AMPB, maleic hydrazide (MH) and mixtures thereof were sprayed by foliar application to Japanese privet (*Ligustrum japonica* Thunb., hereinafter referred to as I'), mokkoku (*Ternstroemia japonica* Thunb., hereinafter referred to as J') and Japanese hawthorn (*Rhaphiolepsis umbellata* Makino var. Mertensii Makino, hereinafter referred to as K') in amount of 100 liter per 10 are. Each spraying solution contained 0.1% of polyoxyethylene octylphenyl ether as the surfactant.

The application and the investigation were carried out on December 14, and May 22 of the next year, respectively, and the reproduction-inhibiting effect was determined in accordance with the same evaluation standard as in Example 1. The results are shown in Tables 14 and 15.

TABLE 14

| Concentration (%) | I' | J' | K' |
|---|---|---|---|
| L-AMPB Na 0.125 | 4 | 5 | 5 |
| L-AMPB Na 0.25 | 5 | 5 | 5 |
| MH 0.5 | 1 | 1 | 1 |
| MH 1.0 | 2 | 1.5 | 1.5 |
| MH 2.0 | 2.5 | 2 | 2 |
| L-AMPB Na 0.125 + MH 0.5 | 5 | 5 | 5 |
| L-AMPB Na 0.125 + MH 1.0 | 5 | 5 | 5 |
| L-AMPB Na 0.125 + MH 2.0 | 5 | 5 | 5 |
| L-AMPB Na 0.25 + MH 0.5 | 5 | 5 | 5 |
| L-AMPB Na 0.25 + MH 1.0 | 5 | 5 | 5 |
| L-AMPB Na 0.25 + MH 2.0 | 5 | 5 | 5 |

TABLE 14-continued

| Concentration (%) | I' | J' | K' |
|---|---|---|---|
| None | 0 | 0 | 0 |

TABLE 15.

| Concentration (%) | I' | J' | K' |
|---|---|---|---|
| DL-AMPB Na 0.25 | 4 | 5 | 5 |
| DL-AMPB Na 0.5 | 5 | 5 | 5 |
| MH 0.5 | 1 | 1 | 1 |
| MH 1.0 | 2 | 1.5 | 1.5 |
| MH 2.0 | 2.5 | 2 | 2 |
| DL-AMPB Na 0.25 + MH 0.5 | 5 | 5 | 5 |
| DL-AMPB Na 0.25 + MH 1.0 | 5 | 5 | 5 |
| DL-AMPB Na 0.25 + MH 2.0 | 5 | 5 | 5 |
| DL-AMPB Na 0.5 + MH 0.5 | 5 | 5 | 5 |
| DL-AMPB Na 0.5 + MH 1.0 | 5 | 5 | 5 |
| DL-AMPB Na 0.5 + MH 2.0 | 5 | 5 | 5 |
| None | 0 | 0 | 0 |

EXAMPLE 10

Sodium salts of DL-AMPB or L-AMPB, or glyphosate were sprayed by foliar application in amount of 100 liter per 10 are to flatstage (*Cyperus serotinus* Rottb.) grown in 1/5000 are Wagner pots, in the end of October. Each spraying solution contained 0.1% of polyoxyethylene octylphenyl ether as the surfactant. After three months, the tubers were cut off and subjected to germination test in tall petri dishes. 21 days after initiation of the germination test, the germination-inhibiting effect (0: no harm, 5: no emergence) was determined. The results are shown in Table 16.

TABLE 16.

| Concentration (%) | Germination-inhibiting effect |
|---|---|
| DL-AMPB Na 0.1 | 5 |
| DL-AMPB Na 0.3 | 5 |
| L-AMPB Na 0.1 | 5 |
| L-AMPB Na 0.3 | 5 |
| glyphosate 0.1 isopropylamine salt | 3 |
| glyphosate 0.3 isopropylamine salt | 5 |
| None | 0 |

We claim:

1. A method for controlling perennial weeds which comprises applying herbicidal compositions containing a herbicidally effective amount of the L-isomer of a compound of the formula

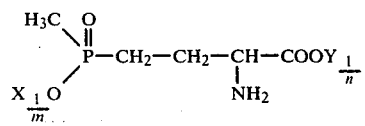

wherein X and Y are the same or different and each represents a hydrogen atom, a mono- or di-valent metal atom, a mono-, di- or tri-lower-alkylammonium, a mono-, di- or tri-ethanolammonium, or a mono-, di or tri-lower-alkenylammonium, and m and n represent valencies of X and Y, respectively or an acid-addition salt thereof to land selected from the group consisting of crop land, non-crop land, orchard, forest land and meadow.

2. The method of claim 1, wherein the perennial weeds are selected from the group consisting of azumanezasa (*Pleioblatus chino,* Makino), miyakozasa (*Sasa niponica* Makino et Shibata), needle grass (*Imperata cylindrica* (L) Beauv), eulalia (*Miscanthus sinensis* Andress.), mizugayatsuri (*Cyperus serotinus*), wormwood (*Artemisia princeps* Pamp.), bitter dock, yabugarashi (*Cayratia japonica* Houtt.), kudzu (*Pueraria thunbergiana* Benth.), warunasubi (*Solanum carolinense* (L)), inuwarbai (*Athyrium niponicum* Hance) and hedge bindweed.

3. The method of claim 2, wherein the perennial weeds are selected from the group consisting of needle grass (*Imperata cylindrica* (L) Beauv.), eulalia (*Miscanthus sinensis* Andress.), mizugayatsuri (*Cyperus serotinus*), wormwood (*Artemisia princeps* Pamp), bitter dock, kudzu (*Pueraria thunbergiana* Benth.) and inuwarabi (*Athyrium niponicum* Hance).

4. The method of claim 1 wherein said herbicidal compositions are applied to Japanese cypress (*Chamecyparis obtusa Eudl.*) forest land to control perennial weeds without phytotoxicity to said Japanese cypress.

5. The method of claim 1 wherein said herbicidal compositions are applied to perennial weeds in autumn to control the emergence of new buds thereof during the following spring.

6. The method of claim 1 wherein X and Y are each independently selected from the group consisting of a hydrogen atom, sodium atom, potassium atom, isopropylammonium, n-butylammonium or ammonium.

7. A method for controlling brush which comprises applying herbicidal compositions containing a herbicidally effective amount of the L-isomer of a compound of the formula

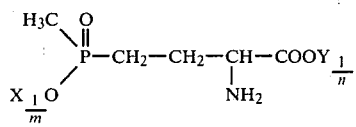

wherein X and Y are the same or different and each represents a hydrogen atom, a mono- or divalent metal atom, a mono-, di- or tri-lower-alkylammonium, a mono-, di or tri-ethanolammonium, or a mono-, di- or tri-lower-alkenylammonium, and m and n represent valencies of X and Y, respectively or an acid-addition salt thereof to land selected from the group consisting of crop land, non-crop land, orchard, forest land and meadow.

8. The method of claim 7, wherein said brush is selected from the group consisting of kumaichigo, kiichigo (*Rubus palmatsu* Thunb. *forma coptophyllus* Makino), chestnut, Japanese bush cranberry, oak, Japanese pickly ash (*Xanthoxylum piperitum DC.*), lace shrub (*Stephanandra incisa Zabel*), yamazakura (*Prumus donarium Sieb. var. spontanae* Makino) and torch azalea.

9. The method of claim 7 wherein said herbicidal compositions are applied to Japanese cypress (*Chamecyparis obtusa Eudl.*) forest land to control brush without phytotoxicity to said Japanese cypress.

10. A method according to claim 7 wherein said herbicidal compositions are applied to brush in autumn to control the emergence of new buds thereof during the following spring.

11. The method of claim 7 wherein X and Y are each independently selected from the group consisting of a hydrogen atom, sodium atom, potassium atom, isopropylammonium, n-butylammonium or ammonium.

* * * * *

UNITED STATES PATENT AND TRADEMARK OFFICE
CERTIFICATE OF CORRECTION

PATENT NO. : 4,265,654
DATED : May 5, 1981
INVENTOR(S) : TETSUO TAKEMATSU et al

It is certified that error appears in the above—identified patent and that said Letters Patent is hereby corrected as shown below:

On the Title page:

Abstract, line 1, before "2-Amino-4-methylphosphinobutyric", insert --2-Amino-4-(hydroxy)(methyl)phosphinoylbutyric acid, which earlier nomenclature referred to as--.

Abstract, line 4, delete "than" and insert --as--.

Column 3, line 1, before "The", insert --Said AMPB which was named 2-amino-4-methylphosphinobutyric acid hereinbefore is by the latest nomenclature named 2-amino-4-(hydroxy)(methyl)phosphinoylbutyric acid in accordance with the International Union Of Pure And Applied Chemistry, "Nomenclature Of Organic Chemistry", pages 384, 385 and 403 (1979 Edition).--.

UNITED STATES PATENT AND TRADEMARK OFFICE
CERTIFICATE OF CORRECTION

PATENT NO. : 4,265,654
DATED : May 5, 1981
INVENTOR(S) : TETSUO TAKEMATSU et al

It is certified that error appears in the above—identified patent and that said Letters Patent is hereby corrected as shown below:

Column 3, line 28, rewrite "immportant" as --important--.

Column 3, line 29, rewrite "solved" as --solve--.

Column 8, line 6, rewrite "mehtyl" as --methyl--.

Column 24, line 62, after "atom," insert --ammonium,--.

Column 26, line 10, after "atom," insert --ammonium,--.

Signed and Sealed this

Fourth Day of May 1982

[SEAL]

Attest:

GERALD J. MOSSINGHOFF

Attesting Officer    Commissioner of Patents and Trademarks